United States Patent [19]

Goodson

[11] Patent Number: 4,764,377
[45] Date of Patent: Aug. 16, 1988

[54] INTRA-POCKET DRUG DELIVERY DEVICES FOR TREATMENT OF PERIODONTAL DISEASES

[75] Inventor: J. Max Goodson, Cambridge, Mass.

[73] Assignee: The Forsyth Dental Infirmary for Children, Boston, Mass.

[21] Appl. No.: 15,521

[22] Filed: Feb. 13, 1987

Related U.S. Application Data

[63] Continuation-in-part of Ser. No. 539,823, Oct. 7, 1983, abandoned.

[51] Int. Cl.⁴ .............................................. A01N 18/00
[52] U.S. Cl. ................................... 424/435; 424/443; 424/444; 432/80
[58] Field of Search ................. 421/435, 443, 448, 449

[56] References Cited

U.S. PATENT DOCUMENTS

| | | | |
|---|---|---|---|
| 2,991,224 | 7/1961 | Bell | 424/28 |
| 3,386,440 | 6/1968 | Cohen | 424/28 X |
| 3,388,704 | 6/1968 | Kurtz | 128/335.5 |
| 3,674,901 | 7/1972 | Shepherd | 424/27 |
| 3,700,685 | 10/1972 | Hoff et al. | 260/309 |
| 3,754,332 | 8/1973 | Warren, Jr. | 424/28 X |
| 3,849,185 | 11/1974 | Shepherd | 117/161 |
| 4,020,558 | 5/1977 | Cournut et al. | 604/892 X |
| 4,024,871 | 5/1977 | Stephenson | 128/335.5 |
| 4,039,653 | 8/1977 | DeFoney et al. | 424/28 X |
| 4,110,429 | 8/1978 | Gaffar et al. | 424/54 |
| 4,136,162 | 1/1979 | Fuchs et al. | 424/27 X |
| 4,144,317 | 3/1979 | Higuchi et al. | 424/21 |
| 4,175,326 | 11/1979 | Goodson | 424/14 X |
| 4,205,061 | 5/1980 | Vidra | 424/55 |
| 4,224,308 | 9/1980 | Gaffar et al. | 424/49 |
| 4,251,507 | 2/1981 | Olson | 424/49 |
| 4,303,765 | 12/1981 | Musch et al. | 525/343 |
| 4,304,765 | 12/1981 | Shell et al. | 424/22 |
| 4,568,535 | 2/1986 | Loesche | 424/19 |

FOREIGN PATENT DOCUMENTS

| | | |
|---|---|---|
| 498575 | 6/1977 | Australia . |
| 527826 | 1/1980 | Australia . |
| 532530 | 7/1980 | Australia . |
| 0022289 | 6/1980 | European Pat. Off. . |
| 0063604 | 9/1981 | European Pat. Off. . |

OTHER PUBLICATIONS

J. M. Goodson et al, "Monolithic Tetracycline-Containing Fibers for Controlled Delivery to Periodontal Pockets", J. Periodontology, 54, pp. 575–579 (1983).

Exerpts from "The Polymer Handbook", 2nd Edition, J. Brandrup and E. H. Immergut, Editors, John Wiley & Sons (1975).

Computer printouts concerning patents referred to in, or citing, U.S. Pat. Nos. 4,024,871 by Stephenson and 3,849,185 by Shepherd.

Primary Examiner—Thurman K. Page
Assistant Examiner—L. R. Horne
Attorney, Agent, or Firm—Weingarten, Schurgin, Gagnebin & Hayes

[57] ABSTRACT

Therapeutic agent delivery devices and methods for using them in treatment of dental disease are disclosed. In the treatment of periodontal disease, a therapeutic agent such as tetracycline mixed in a polymeric matrix such as ethylene vinyl acetate copolymer is packed into the area to be treated and kept in place for a suitable time, during which the therapeutic agent diffuses out of the polymeric matrix, providing continuous therapy for the treatment site.

5 Claims, 2 Drawing Sheets

INTRA-POCKET DRUG DELIVERY DEVICES FOR TREATMENT OF PERIODONTAL DISEASES

This application is a continuation-in-part of application Ser. No. 539,823, filed Oct. 7, 1983, now abandoned.

BACKGROUND OF THE INVENTION

1. Field of the Invention

This invention pertains generally to products and processes for treating diseases of the mouth, and particularly, to treatment of periodontal diseases.

2. Description of the Prior Art

Periodontal disease is a condition caused by a pathogenic microbial ecology established within the gingival sulcus which deepens to become a periodontal pocket. This microbial ecology, located deep within the periodontal pocket, differs greatly from that of the superficial oral environment by being more anaerobic, having a larger number of Gram negative organisms, and having a greater proportion of motile species.

Several factors impede the diffusion of medicinal agents when applied to the superficial periodontal tissues. Anatomically, the gum tissue is closely adapted to the neck of the teeth, mechanically restricting the diffusional pathway. In addition, a fluid termed gingival crevice fluid, with the approximate composition of plasma, permeates the periodontal environment and is continually produced by the diseased periodontal tissues at a rate of 10 to 100 microliters per hour. This fluid, emanating from the diseased pocket lining, creates a net outward flow further impeding the introduction of medications from superficially applied drug delivery devices. These interferences are sufficiently effective to insulate the pocket environment to the extent that saliva does not penetrate, and topically applied medicinal agents have been found largely ineffectual in the treatment of established periodontitis.

Although mouth rinses may be effective in the reduction of superficial gingivitis resulting from poor home care procedures, the effective radius of action of these agents does not extend to the periodontal pocket. Introduction of antibacterial agents in solution form into the periodontal pocket is similarly ineffective due to the rapid clearance of such agents so that the duration of contact at the active site is minimal.

Conventional therapy for periodontal diseases, as first enunciated by Pierre Fauchard in 1746 in his book entitled "The Surgeon Dentist, a Treatise on Teeth," involves the mechanical removal of bacterial plaques and accumulations from the periodontal pocket at periodic intervals. This may include periodontal surgery to achieve access and to recontour damaged tissues. These procedures require a high degree of technical expertise from the practioners of the art, are expensive, and often result in pain, extensive bleeding, and general discomfort on the part of the patient so treated. Since these procedures provide, at best, only temporary reduction in bacterial populations, they must be repeated at regular intervals to be effective. As discussed by Lindhe and coworkers in "Healing Following Surgical/Non-Surgical Treatment of Periodontal Disease" in the *Journal of Clinical Periodontology*, vol. 9, pages 115–128, the frequency of repetion needed for optimal results may be as high as once every two weeks.

Methods for administering drugs for periodontal therapy have heretofore largely been concerned with superficial application. For example, long-acting capsules or tablets held in the mouth (see U.S. Pat. No. 3,911,099); buccal implants for releasing drugs into the saliva (see U.S. Pat. No. 4,020,558); topically applied gels (see U.S. Pat. No. 3,679,360); topically applied drug-containing bandages (see U.S. Pat. No. 3,339,546); a drug-containing plastic hardenable mass (see U.S. Pat. No. 3,964,164); a medicated periodontal dressing (see U.S. Pat. No. 3,219,527); a topical dressing composed of a finely divided particulate carrier and suspended medicinal agents (see U.S. Pat. No. 3,698,392); a bandage for covering moist mucosal surfaces (see U.S. Pat. No. 3,339,546); a microencapsulated liquid droplet formation for topical application to the gums of dogs and other animals (see U.S. Pat. No. 4,329,333); and foam-film devices containing medication (see U.S. Pat. No. 3,844,286). In addition, several fibrous forms for superficial medication have been described, including impregnated or drug-releasing forms of dental flows (see U.S. Pat. Nos. 3,417,179, 2,667,443, 2,748,781, 3,942,539); solid absorbable fibers of polyglycolic acid with medicants incorporated therein (see U.S. Pat. No. 3,991,766); and cellulose acetate hollow fibers (see U.S. Pat. No. 4,175,326).

Systemic antibiotic therapy for periodontal infections has also been used. In this instance, the objective is to eliminate or suppress growth of specific pathogenic species. Systemic administration of antibiotics starts by selection of the antibiotic with appropriate antibacterial spectrum. Thus, for example, one might administer penicillin to eliminate Gram positive anaerobe infections, metranidazole to eliminate Gram negative anaerobe infections, and tetracycline to eliminate actinobacillus infections. If effective, specific organisms sensitive to the relatively low concentrations of antibiotic achieved by this mode of therapy (ca. 2–10 ug/ml) will be selectively eliminated. Because of the low concentrations of antibiotic achieved by systemic administration and the relative high levels of bacterial resistance associated with periodontal pathogens, the clinical success of this mode of therapy has been poor, as discussed by Genco in "Antibiotics in the Treatment of Human Periodontal Diseases," in *J. Periodontology*, vol. 52, pages 546–558 (1981).

Thus, it appears that none of the previously disclosed procedures has led to an acceptable system for delivering optimally effective levels of antibacterial substances to the site of periodontal disease activity. In addition, it appears that delivery of optimal concentrations of any medicinal agent to disease sites within the periodontal pocket has not been addressed.

SUMMARY OF THE INVENTION

A therapeutic agent delivery device is placed within the periodontal pocket in such a manner that the diseased pocket regions come in intimate contact with it. The active agent is thus released at the site of disease, eliminating the variability inherent in long diffusional pathways associated with superifical or systemic treatments. A periodontal pack or other mechanical retaining system keeps the delivery system in this optimal position for the desired period of time. By designing release characteristics of the drug delivery system to provide sustained delivery over a period of days to months, a duration of contact and drug concentration is achieved which results in complete inhibition of all bacterial growth within the periodontal pocket. Upon removal of the therapeutic agent delivery device and the mechanical maintenance device, the periodontal pocket, now devoid of microorganisms, will repopulate in large part from the adjacent oral environment, a microbial population which constitutes organisms of low potential pathogenicity in the periodontal environment. As a result of the altered microbial population, clinical signs of healing are evidenced, including decreased redness, decreased bleeding, reduction of halitosis, elimination of suppuration, elimination of pain, and regeneration of lost connective tissue support for the tooth.

The design and application of devices which employ this therapeutic principle represent a novel approach to the treatment of periodontal disease with the advantages of longer-lasting effectiveness and less pain in application than conventional therapeutic procedures. A therapeutic agent delivery and maintenance system suitable for continuously delivering a pharmacologically-effective level of therapeutic agent to the site of a periodontal infection within a periodontal pocket and maintaining it there includes therapeutic material and biocompatible polymeric material having a glass transition temperature less than 37° C. The polymeric material contains the therapeutic material impregnated in the polymeric matrix. The polymeric material is permeable to the therapeutic material so that the latter can diffuse out over a substantial period of time. The polymeric matrix containing the therapeutic agent is in the form of a fiber having a diameter in the range from 0.1 to about 1 mm, and this fiber is sufficiently flexible and formable to conform readily to the periodontal site to be treated. Included as part of the therapeutic agent delivery and maintenance system is an appropriate means for maintaining the therapeutic agent-containing delivery device within the periodontal pocket in contact with the site to be treated. This function is performed by a periodontal pack or other suitable mechanical devices which in use are placed over the top of the periodontal pocket between the gum and the tooth, and maintain the fiber within the pocket while simultaneously limiting diffusion of therapeutic agent from the periodontal pocket.

A method for treating periodontal disease employing the claimed therapeutic agent delivery and maintenance system involves placing the above-described fiber-shaped therapeutic agent delivery device within a periodontal pocket directly in contact with the infected site to be treated, and maintaining it there for a predetermined time of treatment by using a retaining device separate from the therapeutic agent delivery device to cover the top of the periodontal pocket and the fiber therein, this retaining device also simultaneously serving to limit diffusion of the therapeutic agent from the pocket.

DETAILED DESCRIPTION OF THE INVENTION

Figure 1:
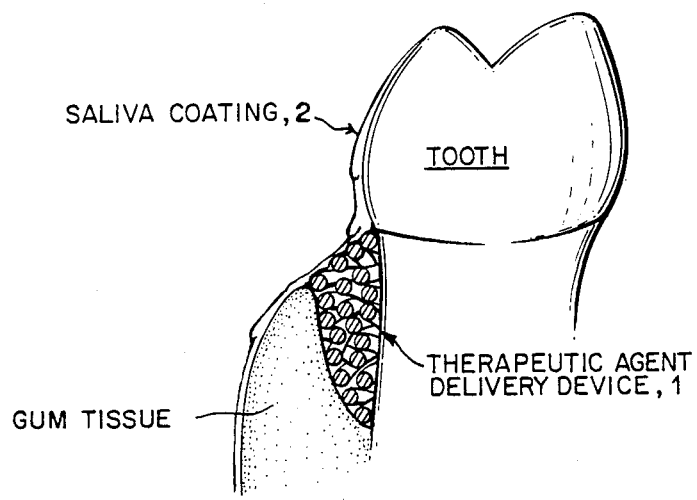
FIG. 1 illustrates a therapeutic agent delivery device (1) designed to lie totally within the periodontal pocket between gum and tooth. It is held in place by mechanical locking, by elastic retention, by adhesive properties intrinsic to the plastic, or by a suitable adhesive. This delivery system is in contact with saliva (2), to which some of the therapeutic material can diffuse.
Figure 2:
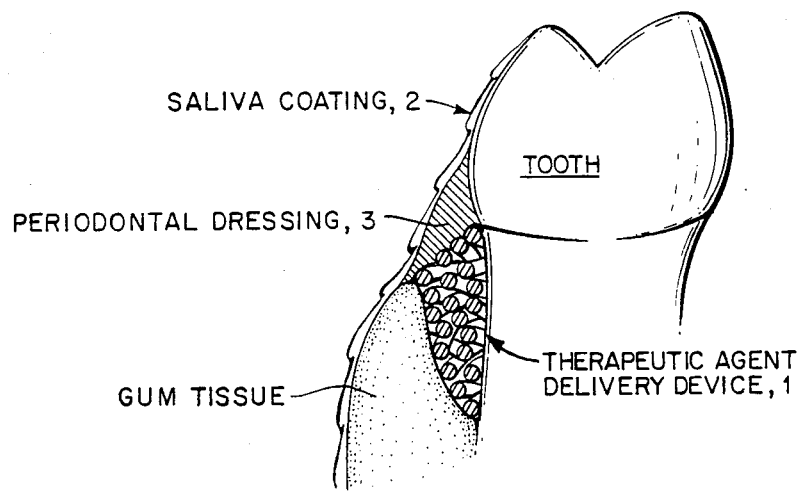
FIG. 2 illustrates a form of therapy in which an inert conforming dressing (3) overlies the delivery device (1) to hold the device in place and limit diffusional loss of the therapeutic agent into the salivary compartment.
Figure 3:
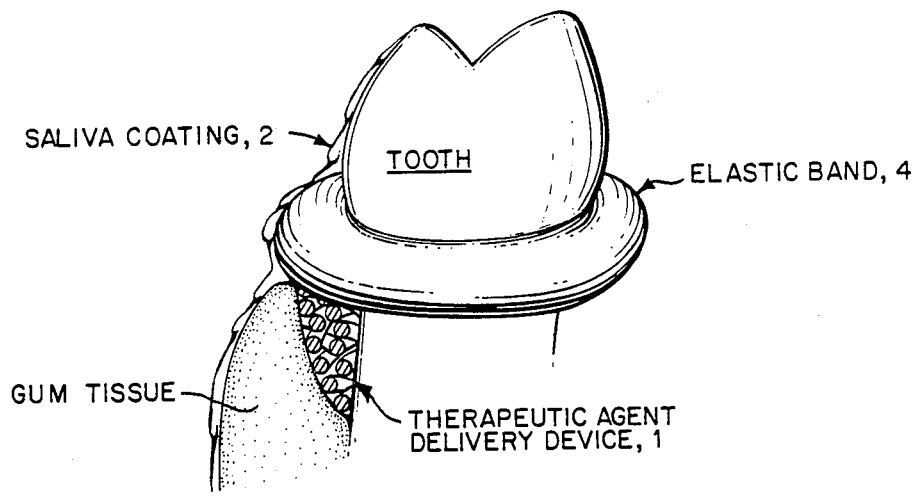
FIG. 3 illustrates an alternative form of mechanical retention, in which an elastic band of bicompatible material (4) serves to occlude the pocket orifice and mechanically retain the delivery device.
Figure 4:
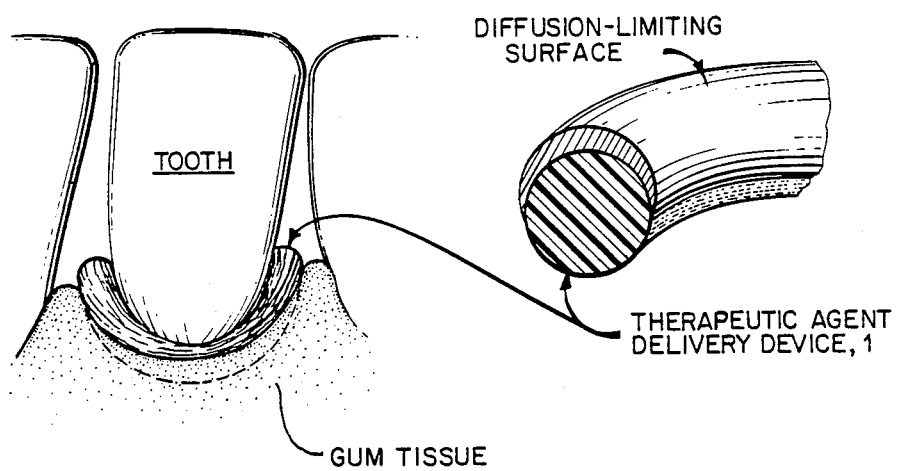
FIG. 4 illustrates an alternative form in which an anular formed elastic therapeutic agent delivery device with a diffusion-limiting outer surface is designed to lie wholly or in part in a shallow periodontal pocket or sulcus.

The invention relates to a method for treating periodontal disease by means of a therapeutic agent delivery device placed within the periodontal pocket so that release of the therapeutic agent occurs in the immediate vicinity of the disease process. As the volume of distribution is limited to the total volume of gingival crevice fluid produced within the periodontal pocket, relatively high concentrations of therapeutic agent are developed in the pocket by devices with small therapeutic agent reservoir capacities. The small amount of therapeutic agent required under these conditions, typically a few milligrams, greatly reduces the effect of the therapeutic agent at distal sites within the body, thereby greatly decreasing the potential for systemic side effects. By establishing local concentrations of an antibacterial agent sufficient to inhibit growth of all bacteria within the pocket, development of drug resistant strains in minimized. The potential for encouraging the development of drug-resistant pathogens is further minimized by the relatively short duration required to achieve the desired effect, typically on the order of three to ten days. By this procedure, therapeutic agent delivery devices containing a few milligrams of therapeutic agent are capable of rendering effects greater than would be expected by the same drug used at much higher doses by other routes of administration. This principle results in an unexpectedly high degree of effectiveness from the comparatively small amount of drug utilized.

The use of a periodontal dressing or other mechanical retaining and/or diffusion-limiting device further enhances therapeutic effectiveness. This aspect of the method of treatment has the primary function of maintaining the delivery device in an optimal position to render its effect. A second function is to reduce diffusion of therapeutic agent and therefore reduce loss of the agent into the saliva. The restriction of therapeutic agent diffusion into saliva further reduces possible side effects which could conceivably occur in the oral cavity or in the gastrointestinal tract.

The local delivery devices useful in the invention comprise therapeutic materials in a matrix of bicompatible semipermeable polymeric material. By proper selection of the polymeric material and therapeutic material, blends may be obtained from which the therapeutic material will diffuse at a controlled rate over selected periods of time.

A wide variety of semipermeable biocompatible natural or synthetic polymers, such as collagen, cellulosic polymers, glycolic acid polymers, methacrylate polymers, ethylene vinyl acetate polymers, ethylene vinyl alcohol copolymers, polycaprolactone, etc., may provide the polymeric substance for the local delivery device. Additionally, polyurethanes and polylactides may be employed. These materials may be fabricated into a variety of shapes, including slabs, strips, films, ribbons, or fibers, and may have various consistencies, including solids, gels, plastic, granular aggregates, microsphere preparations, and spongy forms capable of being formed or introduced into the periodontal pocket.

The therapeutic agent delivery device is preferably in the shape of a fiber having a diameter of about 0.1 to about 1 mm. For best results, this fiber should be sufficiently formable and flexible to conform to the site to be treated, and this requirement in turn makes it necessary to use soft polymers, typically having glass transition temperatures Tg less than about 37° C. Preferred polymers useful in the invention have glass transition temperatures less than about 32° C., while a particular ethylene vinyl acetate copolymer employed in trials and found highly efficacious has a glass transition temperature less than 28° C. Those skilled in the art will known that the glass transition temperature is that temperature below which the molecules of the polymer are restricted in their freedom of rotational motion, thereby causing the polymer to be rather stiff, and above which the molecules of the polymer have acquired sufficient thermal energy for isomeric rotational motion or for significant tortional oscillation to occur about most of the bonds in the main chain which are capable of such motion, thus causing the polymer to be soft and flexible. Polymers having glass transition temperatures below body temperature (approximately 37° C.) are conformable, relatively soft, and flexible, but on the other hand exhibit quite low tensile strengths. Thus, for example, such low glass transition value materials are not suitable for use in applications where any substantial degree of strength is required, such as for manufacture of sutures or fabrics. Although products such as sutures and fabrics have been manufactured of synthetic polymeric fibers containing certain antibacterial agents, such products are made using polymeric materials having glass transition temperatures above body temperature, to assure sufficient strength.

Table I below compares the physical properties of the polymeric material ethylene vinyl acetate, characterized by a low transition temperature, with three polymers having high glass transition temperatures and used for their structural advantages. Clearly, low glass transition temperatures are associated with low values of tensile strength and tensile modulus, and with correspondingly high values of elongation at break. In other words, a material having a low glass transition temperature is not very strong and stretches significantly before breaking. By contrast, the data shown for polyethylene terephthalate, polytetrafluoroethylene, and polyamides illustrates that materials having glass transition temperatures of 40° C. and above have substantially higher tensile strengths and tensile modulus values and substantially lower values of elongation at break than low glass transition materials. Most commercially available sutures are made of the latter four materials listed in the first column of the table, in keeping with the demonstrated high strength of these materials. Polymeric materials for use in the fibers of the present invention, however, should not be made of polymers having glass transition temperatures above body temperature (37° C.) because such fibers are too stiff and inflexible to be easily folded and packed into a periodontal pocket, and if forced into such a pocket would produce discomfort, and would adapt poorly to the contours of a periodontal pocket. In addition, such fibers would be difficult to pack into the pocket in the first instance because of their inflexibility.

TABLE I

| | Glass Transition Temp. (°C.) | Tensile Strength (psi) | Elongation at break (%) | Tensile Modulus (psi at 23° C.) |
|---|---|---|---|---|
| Ethylene vinyl acetate (Elvax 40) | <28 | 650 | 1450 | 300 |
| Polyethylene terephthalate (Dacron) | 67 | 25,000 | 75 | 20,400 |
| Polytetrafluoroethylene (Teflon) | 126 | 39,200 | 200–400 | 4,210 |
| Poly amides | | | | |
| Nylon 6 | 40–87 | 11,600 | 20–25 | 435,000 |
| Nylon 66 | 50 | 13,050 | 20–25 | 479,000 |
| Polypropylene | 30–80 | 4,300–5,600 | 500–900 | 150,000–249,000 |

It is recognized that in the fabrication of local delivery devices, certain inert substances may be included to modify the delivery characteristics or serve as carriers of the active agent, including solvents, suspending agents, surfactants, viscosity-controlling agents, complexing agents, antioxidants, antibacterials, and other pharmaceutically acceptable materials which may be employed to solubilize or stabilize the materials in the polymeric matrix and control the rate of permeation or the action of the materials after permeation.

This invention is not limited to the use of antibacterial agents alone. A wide variety of therapeutic agents may be used in the invention. Some therapeutic agents which are amenable to delivery by this means and are potentially of value for periodontal therapy, incude (but are not limited to) antibacterial agents such as iodine, sulfonamides, mercurials, bisbiguanides, or phenolics; antibiotics such as tetracycline, neomycin, kannamycin, metranidazole, or canamycin; anti-inflammatory agents such as indomethacin, euginol, or hydrocortisone; immune-suppressive or stimulatory agents such as methotrexate or levamasole; dentinal desensitizing agents such as strontium chloride or sodium fluoride; odor masking agents such as peppermint oil or chlorophyll; immune reagents such as immunoglobulin or antigens; local anesthetic agents such as lidocaine or benzocaine; nutritional agents such as amino acids, essential fats, and vitamin C; antioxidants such as alphatocopherol and butylated hydroxy toluene; lipopolysaccharide complexing agents such as polymyxin; or peroxides such as urea peroxide. It is recognized that in certain forms of therapy, combinations of these agents in the same delivery system may be useful in order to obtain an optimal effect. Thus, for example, an antibacterial and an anti-inflammatory agent may be combined in a single delivery system to provide combined effectiveness.

The means for mechanical maintenance of the delivery system (hereafter, maintenance system) generally serves not only to hold the therapeutic agent delivery device in place, but also to prevent or reduce diffusion of the therapeutic agent out of the periodontal pocket. It can take a variety of forms; for example, an inert periodontal dressing, an elastic band of suitable biocompatible material, an elastic sheet, an adhesive film or gel such as n-butylcyanoacrylate, or a metallic or polymeric cover. It may be biodegradable, thus eventually allowing the therapeutic agent delivery device to be washed out of the periodontal pocket by gingival fluid flow, thereby terminating therapy. In addition, it may itself provide a therapeutic agent delivery function which could, for example, serve to decrease bacterial or fungal accumulations, reduce local inflammation, or mask mouth odors. The maintenance system can be fastened in place by any suitable means, including self-adhesion, melting, cementing, crimping, etc.

The maintenance system may also be intrinsic to the therapeutic agent delivery device for example, where the delivery device itself has adhesive properties or possesses a springiness which would cause it to be retained in the periodontal pocket once it has been inserted into the pocket in a compressed state.

Experimental determination of the concentration of tetracycline necessary to suppress the growth of all cultivable periodontal microorganisms:

Samples containing periodontal organisms taken from deep periodontal pockets of 5 patients were transferred to 10 ml of pre-reduced Ringer's solution, dispersed by 10 seconds of sonic oscillation at an amplitude of 10 microns, and dilutions of 1:20, 1:100, and 1:1000 were prepared. One-tenth milliliter of each dilution was streaked on trypticase soy agar containing 5% sheep blood and 0.3 ug/ml menadione in petrie dishes. Identical plates were prepared containing 1, 8, 32, and 64 micrograms/milliliter of tetracycline hydrochloride. Inoculated plates were incubated at 35° C. in an anaerobic atmosphere at 80% nitrogen, 10% hydrogen, and 10% carbon dioxide for 5 to 7 days. Plates from dilutions providing separated colony growth were selected for counting to determine the total colony forming units on primary medium and each associated tetracycline-containing medium. Percentages of organisms grown at each concentration were computed. Values of 21.2%, 3.6%, 0.08%, and 0% were found on plates containing 1, 8, 32, and 64 micrograms/millileter tetracycline respectively. These observations indicate that no cultivable periodontal organisms grow at tetracycline concentrations of 64 micrograms/milliliter, thereby establishing the primary design parameter for a local drug delivery system for periodontal therapy which would suppress growth of all cultivable periodontal microorganisms with continuous exposure of the organisms to tetracycline.

Preparation of a therapeutic agent delivery device containing tetracycline as the therapeutic agent:

The chamber of a Tinius Olsen Extrusion Plastometer, with a spinneret inserted, was preheated to approximately 180° C., a temperature below the temperature at which tetracycline hydrochloride decomposes. It was then loaded with a mixture of 25% by weight of tetracycline hydrochloride in ethylene vinyl acetate copolymer (45% vinyl acetate, melt index 7.5 g/10 min), and an extrusion ram with weights attached was inserted into the chamber to compress the mixture while it equilibrated. After equilibration, additional weights were added to the ram to force the molten material through the spinneret. As the material was extruded, it cooled to form fibers which were collected in loose coils. Fibers so prepared were approximately 0.5 mm in diameter, contained about 300 ug of tetracycline hydrochloride per centimeter, and were elastic and slightly tacky.

In vitro release of tetracycline hydrochloride from ethylene vinyl acetate copolymer fibers:

Triplicate samples of ethylene vinyl acetate copolymer fibers containing about 300 ug of tetracycline hydrochloride per cm were immersed in separate flasks containing 25 or 50 ml aliquots of deionized water, the containers were sealed, and the mixtures were agitated gently at 37° C. on a shaking water bath. Three-ml aliquots of the receiving fluid were periodically sampled and assayed for tetracycline hydrochloride by measuring the absorption peak at 276 nm on a Perkin-Elmer 575 spectrophotometer. A 3-ml aliquot of deionized water was added to the receiving fluid of each vessel sampled to replace the volume removed. The amount of tetracycline released was determined from a Beer's Law plot derived from the absorbance of known concentrations of tetracycline hydrochloride. Such tests showed that the fibers tested possessed non-linear release characteristics, sustaining delivery for 9 days under the experimental conditions. The apparent permeability constant obtained from Fick's Law of diffusion as applied to cylindrical geometry was $7.1 \times 10^{-12}$ gm cm$^{-1}$ sec$^{-1}$. The approximation of drug release rate during the first day was 100 ug/cm, and over days 2 through 9 it was approximately 25 ug/cm/day.

Assay for tetracycline in gingival fluid:

Samples of gingival fluid were taken by intracrevicular sampling technique using filter paper strips (Harco periopaper). The relative volume of the sample was measured by the change in dielectric constant of the filter paper (Harco Periotron) and the volume was computed from a standard response obtained from serum. The amount of tetracycline on the filter paper sample was determined by comparing the diameter of inhibition of growth of *Bacillus cereus* caused by the placement of the filter paper on an inoculated plate with the zone of inhibition of standards applied in the same manner. Assay plates were made by inoculating 10 ml of Todd Hewitt broth with *B. cereus* and incubating overnight at 37° C. Mueller-Hinton broth with 1.5% agar was autoclaved and cooled to 50° C. The medium was seeded by adding 2 ml of inoculum to each 100 ml of the cooled broth-agar. Assay plates were made by pipeting 7 ml of the seeded broth-agar medium into 100 mm diameter plastic petri dishes. The assay was performed by placing filter paper strips with either unknowns or standards on the solidified surface of assay plates and incubating at 37° C. overnight.

Tetracycline standards at concentrations of 500, 200, 100, 50, 25 and 12.5 ug/ml were prepared from a 1 mg/ml of stock solution by diluting with pH 7 phosphate with 3.5% bovine serum albumin. A 0.5 ul aliquot of each standard was applied on identical filter paper samples using a 1 ul syringe. The diameter of the zone of inhibition of triplicate or quadruplicate standards was measured to the nearest mm. A standard response function was derived by computing the linear least-squares fit of the diameter of growth inhibition as a function of the fourth root of the amount of tetracycline applied. Analysis of variance of regression of the least-squares fit function for N=66 standard samples indicated that it provided a satisfactory fit to the data. The correlation ratio of the linear regression component was 0.951, indicating that the fitted function explained 95% of the observed variation, deviation from linearity and error accounting for less than 5% of the variation. The average standard deviation of multiple standards was 0.59 mm with no systematic dependence on the amount of tetracycline applied. The fourth order polynominal solution of least-squares fit function was used to compute the amount of tetracycline in gingival fluid samples from the measured zone diameter. This assay provided a measurable response for samples containing between 6 and 250 ng of tetracycline allowing concentrations from 6 to 2500 ug/ml to be determined from sample volumes of 0.1 to 1.0 ul. Concentration was calculated by dividing the nanogram amount as estimated by bioassay by the volume as determined by the gingival fluid meter.

Periodontal treatment; example No. 1:

When a relatively shallow (5 mm) periodontal pocket was packed with ethylene vinyl acetate copolymer containing about 300 ug of tetracycline hydrochloride per centimeter, no covering being employed, an initial concentration of tetracycline, as measured by microbiologic assay of gingival fluid samples, of 650 ug/ml was established with a concentration half-time of 13 hours. In this instance, the treated periodontal pocket was initially populated by approximately $10^{-6}$ spirochetes per standardized microbiologic sample, bled spontaneously, and was characterized by pus formation. Following fiber placement for 10 days, the spirochetal component was no longer detectable by darkfield microscopy. Within one month, the periodontal pocket had healed, leaving a physiologic 3 mm sulcus. All signs of disease disappeared and the site remained clinically healthy during subsequent examination for the following year. These observations indicated that as a result of placement of the therapeutic agent delivery device into the periodontal pocket, a long-term clinical change was associated with a permanent alteration of the microbial ecology of the region.

Periodontal treatment; example No. 2:

The therapeutic agent delivery device of treatment Example 1 was placed into a suppurant, deep (8 mm) periodontal pocket by forcing the fiber into the pocket in such a manner that the irregular pocket geometry was completely filled with the delivery material. This region was then overlaid by a dressing made of zinc-oxide and eugenol. This dressing material, commonly used as an intra-oral bandage by practitioners, was mixed as a combination of liquid and powder which rapidly hardens in the mouth to form an inert mass which conforms to the irregular boundaries of the neck of the tooth and adjacent gum tissue. By so doing, the tetracycline-loaded delivery device already forced deep into the pocket was maintained in close proximity to the active disease site for a total of 10 days. At the time of removal of the periodontal dressing and the underlying drug delivery device the concentration of the tetracycline in gingival fluid was approximately 1000 micorgrams/milliliter (0.1%), indicating that higher levels of drug were maintained over the therapeutic period when the delivery device is covered by a periodontal dressing.

At the time of removal, the periodontal tissues appeared less inflamed. One month later, the pocket depth measured 4 mm, representing a major improvement in connective tissue attachment to the tooth. Over the remaining 6 months of observation, the site continued to appear clinically healthy.

Periodontal treatment; example No. 3:

One periodontal pocket in each of 6 patients was treated as described in Example 2. Microbiologic changes associated with the treatment were evaluated by determining the Gram staining properties of 50 randomly selected isolates derived from blood-agar primary isolation plates incubated in an anaerobic environment. Before treatment, 56% of the organisms isolated were Gram positive; one month later; 71% were Gram positive. These observations indicate that a major microbiologic alteration occurred as a result of the local antibacterial therapy administered in the preceeding month. The significant change in percentage composition indicates that an ecologic alteration has resulted from the therapy.

It should be understood that the description and specific examples given, while indicating preferred embodiments of the invention, are given by way of illustration only, since various changes and modifications within the spirit and scope of the invention will become apparent to those skilled in the art from this description and the accompanying claims.

What is claimed is:

1. A therapeutic agent delivery device suitable for continuously delivering a pharmacologically-effective level of therapeutic agent to the site of a periodontal infection within a periodontal pocket, comprising a therapeutic agent selected from the group consisting of immune-suppressive agents, immune-stimulatory agents, dentinal desensitizers, odor masking agents, immune reagents, antiinflammatory agents, antibacterials, anesthetics, nutritional agents, antioxidants, lipopolysaccharide complexing agents and peroxides; and a biocompatible polymeric material having a glass transition temperature of less than 37° C., said polymeric material containing said therapeutic material impregnated therein and being permeable to said therapeutic material, the combination of said therapeutic agent and said polymeric material being in the form of a fiber having a diameter of about 0.1 to 1 mm, and the polymeric material is a polymer selected from the group consisting of collagen, glycolic acid polymers, methacrylate polymers, and polylactides.

2. The therapeutic agent delivery device of claim 1 wherein the fiber has a diameter of about 0.5 mm.

3. The therapeutic agent delivery device of claim 2 wherein said polymeric material contains 10 to 50 percent by weight of said therapeutic material.

4. The therapeutic agent delivery device of claim 2 wherein said polymeric material for a glass transition temperature less than 32° C.

5. The therapeutic agent delivery device of claim 2 wherein said polymeric material for a glass transition temperature less than 28° C.

* * * * *

UNITED STATES PATENT AND TRADEMARK OFFICE
CERTIFICATE OF CORRECTION

PATENT NO. : 4,764,377
DATED : August 16, 1988
INVENTOR(S) : J. Max Goodson

It is certified that error appears in the above-indentified patent and that said Letters Patent is hereby corrected as shown below:

Column 2, line 19, "flows" should read --floss--.

Column 2, line 27, "suppess" should read --suppress--.

Column 2, line 44, "pages 546-558 (1981)" should read --pages 545-558 (1981).--

Column 3, line 17, "A therapeutic agent delivery" should read --¶ A therapeutic agent delivery--.

Column 3, line 57, "device (1)" should read --device 1--.

Column 3, line 61, "saliva (2)" should read --saliva 2--.

Column 3, line 64, "dressing (3)" should read --dressing 3--.

Column 3, line 64, "device (1)" should read --device 1--.

Column 3, line 68, "bicompatible" should read --biocompatible--.

Column 4, line 1, "material (4)" should read --material 4--.

UNITED STATES PATENT AND TRADEMARK OFFICE
CERTIFICATE OF CORRECTION

PATENT NO. : 4,764,377
DATED : August 16, 1988
INVENTOR(S) : J. Max Goodson

It is certified that error appears in the above-identified patent and that said Letters Patent is hereby corrected as shown below:

Column 4, line 27, "strains in minimized." should read --strains is minimized.--.

Column 6, line 6, "<28" should read --28--.

Column 9, line 45, "1000 micor" should read --1000 micro--.

Signed and Sealed this

Fifteenth Day of June, 1993

Attest:

MICHAEL K. KIRK

Attesting Officer

Acting Commissioner of Patents and Trademarks